United States Patent [19]

Hauck

[11] Patent Number: 4,975,273
[45] Date of Patent: Dec. 4, 1990

[54] ANTI-PERSPIRATIVE REMEDY FOR TREATMENT OF SWEATY FEET AND OTHER SKIN AREAS

[76] Inventor: Walter J. Hauck, 1746 E. Weidman Rd., Rosebush, Mich. 48878

[21] Appl. No.: 198,608

[22] Filed: May 11, 1988

Related U.S. Application Data

[63] Continuation-in-part of Ser. No. 708,330, Mar. 4, 1985, abandoned, which is a continuation of Ser. No. 610,393, May 15, 1984, abandoned, which is a continuation of Ser. No. 424,921, Sep. 27, 1982, abandoned.

[51] Int. Cl.$^5$ .......................... A61K 7/32; A61K 7/48; A61K 7/50
[52] U.S. Cl. ........................................ 424/65; 514/828
[58] Field of Search ............................................ 424/65

[56] References Cited

PUBLICATIONS

L. E. Lamb, M. D. (Ed.), "Your Feet and How to Care for Them," *The Health Letter,* Special Report 43 (1985).
F. Winter, *Handbuch Der Gesamten Parfumerie Und Kosmetik,* Springer-Verlag, Wien, 1952, pp. 190–191, with attached thereto one-page translation into English of the German text thereof, 1986.
L. E. Lamb, M.D., "Dr. Lamb," *Midland Daily News,* Midland, Mich., Monday, Feb. 20, 1989, Section B, p. 2.
Martindale, The Extra Pharmacopolia, 1958, 24th edition, vol. I, pp. 669 to 671.
Winter, Handbuch Der Gesamten Parfumerie Und Kosmetik, 2/1956, pp. 190–191.
Goodman, Cosmetic Dermatology, 1936, pp. 366–367.

*Primary Examiner*—Dale R. Ore
*Attorney, Agent, or Firm*—N. Jerome Rudy; Christopher J. Rudy

[57] ABSTRACT

Feet and pedal portions of the human body are efficaciously conditioned against, and to circumvent and at least substantially preclude or alleviate, the discomfort and distress of offensive and frequently intolerable or at least disagreeable (including, without limitation thereto, the odiferous aspects thereof) sweating and perspiration by a particularized and carefully confined treatment with critically-concentrated aqueous solution(s) of formaldehyde (which, chemically, is $CH_2O$); consequentially followed by a uniquely-sensitive drying procedure to attain satisfactory, longeval cure or remedy of and relief and respite from possible sweaty conditions and circumstances and resultants thereof. If desired and opted, the treatment with comparative excellent results and surprising effect and effectiveness may well be utilized for equivalent abatement(s) and therapeutic value(s) on and for other exposed, superficial, topical, cutaneal or epidermatic application of the precisely-constituted aqueous formaldehyde prescription as may be done and accomplished for other external portions or extremities of the body as are or would be susceptible to curative beneficiation by same.

24 Claims, No Drawings

ANTI-PERSPIRATIVE REMEDY FOR TREATMENT OF SWEATY FEET AND OTHER SKIN AREAS

CROSS-REFERENCES

This is a continuation-in-part of Ser. No. 06/708,330, filed Mar. 4, 1985, abandoned, which is a continuation of Ser. No. 06/610,393, filed May 15, 1984, abandoned, which is a continuation of Ser. No. 06/424,921, filed Sept. 27, 1982, abandoned. Ser. No. 07/159,454 filed Feb. 18, 1988, now abandoned is another continuation-in-part of said Ser. No. 06/610,393.

BACKGROUND OF THE INVENTION

As is well known, perspiration (or sweat) is the saline fluid secreted by the sweat glands. It consists chiefly of water containing: sodium chloride and other salts; nitrogenous substances (including urea); carbon dioxide; and so forth. In man, the sweat glands are of minor importance as excretory channels; the major function of perspiration being to regulate the temperature of the body by cooling as a result of evaporation. A small, rather variable, amount of such secretion and evaporation (called insensible perspiration) goes on constantly. The amount increases with temperature, muscular exertion, etc.

Contrary to a common, non-technical, lay conception, it is also known that sweat is not the culprit in the production of body odor. Rather, the cause for same is the interaction of sweat with certain bacteria that are normally present on the skin. It is this bacterial action on perspiration as formed that results in characteristic body odors.

Three types of glands in the skin produce the secretions called "sweat". Dermatologists and others skilled in the art generally opine and hold to the belief that the normal, fresh secretions of all three types of glands are at least by-and-large substantially, if not completely, odorless in nature. The relatively foul smell or odor associated with sweat and sometimes characterized as "sweaty" does not generate until there occurs the bacterial decomposition of the involvolved perspiratory secretions and exudations.

The potential for odor formation appears to vary and differ following any sudorific activity for each type of involved sweat-producing gland.

Thus, and somewhat suprisingly in the absence of any perspicacious introspection, the major sources of body perspiration, which are the so-called eccrine glands, are relatively unimportant in odor formation upon and after sweating. This is for the simple reason that eccrine sweat notoriously contains only trace amounts of organic material suitable for bacterial action thereupon. The eccrine glands, in this connection, primarily function and assist to control the body temperature. For the most part, they are only active during exercise and exertion; being also performative in response to nervous tension(s), embarrassment and so forth. In certain body areas, such as the palms, soles and underarms, they produce perspiration at lower temperatures and are there readily and particularly capable of activity in association with or consequence to emotional stress.

Apocrine glands, in contrast, produce perspiration that is characterizable in being rich in organic material quite aptly susceptible to vigorous bacterial action. These glands are stimulated predominantly by emotional stress (such as, by way of illustration, fear or pain) and their activity is not noticeably increased in the typical cases by hot weather or exercise.

The third type of skin gland(s) are the sebaceous glands. These produce and provide for skin lubrication an oleaginous material called sebum. At least for people with regular bathing habits and good hygienic discipline, the sebaceous glands play only a relatively minor role insofar as concerns body odor(s).

By deductive procedure in view of what is known about the origin(s) and causation(s) of body odor, there are two (2) ostensible approaches to its prevention and/or cure. These, namely, are to either, or both: (1) impede bacterial action; and/or (2) reduce or minimize sweating. Deodorants and deodorant soaps or detergents and the like are intended to accomplish the first named approach while, on the other hand, antiperspirants and antiperspirant agents are obviously intended for and aimed at accomplishment of the second (althoug, in fact, they may do both of the mentioned functions).

In this connection, some antiperspirants are sometimes called "deodorants" by their manufacturers; even though such products in the commercial market generally include the saving statement "checks perspiration" in association therewith. This indicates that the active ingredients thereof are capable of affecting the sweating function of the body. On the other hand, deodorant soaps, underarm deodorants and the like simple deodorizing materials and agents that merely more or less treat the symtoms of body odor have no contra-sudorific value and more-or-less only serve to mask offensive odor(s). In this, some destructive action of and upon the odor may also be involved. Nonetheless and as has been indicated, a number of so-called "deodorant" products oftentimes contain antiperspirant materials and agents in their composition.

Unfortunately, many of the currently commercially-available antiperspirant concoctions are relatively useless for a proportionately minor group of people who are afflicted with a condition known as hyperhidrosis. This is an innate diaphoretic abnormality which involves the production of large amounts of sweat observed probably more often in and by the underarm glands; even though it is not at all uncommon insofar as concerns such hidrotic phenomenon to be observably-present in and with the sweat glands of either or both the hands or feet. No entirely satisfactory solution for such malady has heretofore been known or available. Medications are almost invariably of no help for such hyperhidrotic occurrences; the sort of abnormal sweating associated therewith being quite often, if not entirely, believed and held by competent authority to be due to localized overactivity of the sympathetic nervous system. In any event and, if not actually experienced, as can readily be appreciated, it is a most unpleasant and rather dreadful condition; being so troublesome in some rare instances as to require undesirable surgery for its correction.

Notwithstanding and even in the absence of the described abnormality, excessive and exaggerated sweating may quite frequently be caused by (and, in fact, is an appropriate pysiological response to) emotional stress and/or physical exercise.

Associable therewith and as a particularized illustration thereof, excessive perspiration of the feet may produce a particularly and distinctively objectionable odor of markedly disagreeable and displeasing olfactory essence. This comes from the specifically and relatively peculiar action of bacteria tending to predominantly inhabit the epidermal or superficial skin layers on the soles the feet.

Additionally and as an aggravating compounding of the immediate distasteful and unhappy effect(s) and consequence(s) of pedal perspiratory residues and retentions, the presence of sweat leavings on the feet oftentimes, if not invariably, encourages and promotes the undesirable and unwanted growth of such fungi and the like organisms as are capable of causing relatively dishabilitating and quite distressing infections or pseudo infections of the sort of acute and chonic inflammations that are typified by and commonly known as "athlete's foot" and so forth, including equivalents thereof.

Prior hereto, the above-indicated and -explained manner and modes of remediation(s) were all that was available to people with a severe and/or extraordinary problem of foot perspiration propensity. Actually (and as good-enough advice under any circumstance attending the mentioned problem), people whose feet tended to undergo excessive perspiration were advised to indulge (whenever possible) in the wearing of sandals on open-weave construction shoes and/or to dress in or with hosiery of cotton or wool rather than nylon (and other synthetics) or silk. Liberal dusting of the feet with plain talc and the like or equivalent powders (many of which are medicated) was and still is urged to help absorb sweat and discourage fungic growth(s).

Dissatisfactorily as it has been, neither nor both of such previous procedures (including use of deodorants and/or anti-perspirants as well as the mechanical varieties of expedients for alleviation of the problem) did little if anything to actually and dispositively check or arrest the production of excess sweating on the feet; being more-or-less designed and adapted to merely and fundamentally treat the involved and attendant symtoms without actually effectively attacking the real source of the problem(s).

Formaldehyde, per se, is a normally gaseous substance which has a melting point of $-92°$ C. and a boiling point of $-21°$ C. Its specific gravity is 0.815. It is most ordinarily available as the so-called Formaldehyde Solution (also known as "Formalin", "Formol" and/or "Morbicid"). This is a solution of about 37 percent by weight, based on total composition weight (i.e., "% by wt.) of formaldehyde gas in water. Usually, about 10–15% by wt. of methanol (i.e., wood alcohol) is added to Formaldehyde Solution compositions as a polymerization inhibitor, although many of the obtainable Formaldehyde Solution(s) are devoid of any such alcoholic additament. Typical of commercial Formaldehyde Solution is that obtained under the "CHEMLINE" Trade Designation from AMERICAN DRUG INDUSTRIES, Inc. of Chicago, Illinois 60671. The indicated Formaldehyde Solution is the same strength as that called "Formalin" and known under such appellation as "Formalin 40%" which signifies that it contains 40 grams of the formaldehyde itself in each 100 milliliters of the solution (the same being equivalent to the indicated 37% by wt. solution). Formaldehye and Formaldehyde Solution are deadly and dangerous poisons which are prudently handled with great care.

Formaldehyde is also commercially available as the so-called Paraformaldehyde, which is polymerized formaldehyde of the formula: $(CH_2O)_n$ and is also known as "Paraform", "Triformol" and "trioxymethylene". Paraformaldehyde, which bears the odor of formaldehyde, dissolves slowly in cold water and more readily in hot water and is obtained by concentrating Formaldehyde Solution.

Formaldehyde Solution and other preparations of formaldehyde find use for disinfection of dwellings, ships, storage houses, utensils, clothing, etc. It has found employment as a germicide and fungicide for plants and vegetables: destroying in this files and other insects. It can prevent mildew and spelt in wheat and certain forms of rot in oats.

Medically, it has found usage as an antiseptic and has also been employed to combat (when applied in 1–2% by wt. aqueous solutions) bacterial infections of mucous membranes. It has further been suggested for utilization in the treatment of various fungus infections of the skin as well as for ivy infections and poisoning and, in very dilute solutions, as a vaginal douch. It has been specifically proposed in strong 20–30% by wt. solutions as: an astringent for the handling of hyperhidrosis; as a keratolytic; and (in concentrations up to as great as 100% by wt.) for eradiction of nevi (such as birthmarks, moles, etc.) and papillomata (such as corns, warts, etc.). In about 2–10% by wt. concentrations, it has been utilized to disinfect surgical instruments and garb (including gloves) and, at about a 10% by wt. level, for disinfection of excreta. Its preservative powers for histological specimens and cadavers is, needless to mention, well known.

Most often, as will hereinafter be more specifically illustrated, the usage of formaldehyde for medical and pharmaceutical purposes has been when the same is contained as an ingredient in specialized and purposively-formulated (often with multiple functions therein inherent) compositions and preparations containing various other ingredients and components designed to ameliorate or in some way beneficiate the formaldehyde-containing formulation.

For veterinary purposes, Formaldehyde Solution and its derivatives and formaldehyde-containing equivalents thereof have been put into external use for such thing as demodectic mange in and of dogs and other skin diseases incident to and inflicted upon the larger animals, such as eczema and acne. Undiluted Formaldehyde Solution has been employed for treating such things as canker of the frog of the horse. Injections of Formaldehyde Solution intraveinously was at one time used in veterinarial treatment of pneumonia. Orally, it was also employed in veterinary practice in administrations as a gastro-intestinal antiseptic in white scours, cattle bloat and mastitis; commonly requiring dosages for horses and cattle of about 8–30 milliliters of the Formaldehyde Solution in well-diluted aqueous preparations.

Formaldehyde solution, per se, exhibits definite human toxicity. Topical application of same may definitely produce an irritant dermatitis. Ingestion may cause severe abdominal pain, hematemesis, hematuria, proteinuria, anuria, acidosis, vertigo, coma and death. Thus, as is readily apparent, its handling and usage must be very prudently and with great caution and care undertaken and done; this re-emphasizing the rule already stated.

By way of illustration of what is involved with the typical formaldehyde concoctions for employment in representative disinfectant, antiseptic and astringent capacities, reference may be had to the relatively complex and multi-componential compositions and formulations disclosed and taught in U.S. Pat. Nos.: 627,642; 628,502; 934,844; 1,920,639; and 2,507,236 to mention only a few of the salient and typical items put forth in prior art concerning use of formaldehyde for medical and the like purposes.

It is noteworthy and significant, however, to discern and take into recognizing full account that the great preponderance of hitherto-followed usages of formaldehyde for therapeutic purposes has intrinsically been along expost-facto and curative or remedial lines rather than in any preventive capacity for any given purpose, including even that pertaining to sudorific or hidrotic problems and occurrences and various medicaments touted therefor.

Consequently and unavoidably, the prior art does not appear to concern itself with preventive techniques or procedures involving in any measure or form formaldehyde usage for the avoidance of problems and difficulties arising from excessive sweating, particularly as concerns foot perspiration and it attendant perplexations and dire influences and effects from both the social nicety and health points of view, in order to have satisfactory and effective control in a direct and straightforward manner that is uncluttered with complication of the excessive sweating phenomena and resultants thereof in the way so indigenuously advantageous and simple as in the present contribution to the art; and very especially as that relates to undue and abnormal sweating of and by the feet of individuals viably and unfortunately plagued with such perplexing conundrum.

FIELD, PURVIEW AND SUMMARY OF THE INVENTION

The instant step forward in the art, in its genesis and as stemming from the discovery on which it is based, concerns the treatment of feet and other non-mucous, sweat-producing body parts and extremities so as to vastly inhibit if not entirely preclude for extended and significant periods of time the production of perspiration thereon and from the sweat glands therewith associated. Thus, the instant invention is calculated to provide a highly desirable new treatment for conditions and external body areas afflicted with the stigma and handicap of profuse sweating, particularly and most noteworthily in connection with the feet, so as to substantially, if not entirely, eliminate the inception of the unhappy consequences and resultants thereof. This, in abidance with the concept and practice of the invention, serves to not only curb, if not to completely dispatch, the production of perspiration on the feet and other external, non-mucous epidermal areas on the body surface but also with utmost benefit to materially diminish and cut-down, if not completely thereupon and thereby prevent, the possibility or likelihood for encounterment, on and of the odor-causing and -provoking action of bacteria on and with normal perspiration (especially when the same is abundant and copiously-obtained on the involved body surface portion, especially in a foot). Exceptionally pronouncedly, "foot-odor" may thus be nicely and satisfactorily controlled so as, for practical purposes, to be quite efficaciously done away with.

The achievement and provision of all that which is indicated are amongst the principle aims goals and objectives of the invention; with even more and additionally other attractive benefits and advantages derivable in and from presently-prescribed practice appearing and becoming increasingly evident in the following revelations.

Thus, the present invention is relevant to all the foregoing; pursuant in same to and as is in fair delineation called for per the recitations in the hereto-ultimately-attached claims, each and every of which for summarizing purposes is and are here reitterated and incorporated by reference.

Suitable materials and formulations, as well as the technical procedures involved, for application and use (encompassing working proportional details, treatment conditions and parameters and other significant specifics) of the invention are also set forth in the ensuing description and specification.

PARTICULARIZED DESCRIPTION AND EXEMPLIFICATION OF THE INVENTION

Unexpectedly facile as it is in realization, the present invention which finds the way to salutary achievement of its aims and goals as are indicated above merely involves the treatment of feet and/or other external, non-mucous, epidermal areas prone for one or another reason to heavy and calamitous sweating and likely aftereffective deleterious (and possibly even detrimental) unpleasant or even loathsome odor and other epidermic inflictions with an aquous solution, in critically-constituted and -proportion formulation, of formaldehyde followed by air-drying of the treated body portion or member at ambient, normal room temperature(s).

The feet or other external skin-bearing portions or parts of the body to be subjected to treatment in accordance with the present invention are preferably—almost to the point of necessity and decidedly most advantageously that way—in a scrupulously clean condition for the treatment. Thorough washing and drying (in any suitable way) just prior to treatment generally assures this. It is important that no foreign matter be present on the skin to be treated if optimum results are to be had. Thus, oils (natural or applied), etc., should be completely removed from the skin surface as a pre-condition to the treatment as well as, as indicated, other dirt, soil and so forth.

The formaldehyde preparation utilized in the treatment is one consisting essentially of, by way of most specific description and specification, one that is made up by the addition of precisely 2 fluid ounces (i.e., "oz." in the English System of Measure) of conventional 37% by wt. Formaldehyde Solution to a pure and uncontaminant-containing water vehicle body that has an exact volume of 1 U.S. gallon or 128 fluid (i.e., "fl.") oz. content in other words, the 2 fl. oz. of Formaldehyde Solution is added to (and not incorporated so as to make up a total of) the 1 gallon volume of water for dispersing and carrying same in the treating solution to be utilized, thus rendering a total volume of prepared treating solution of 130 fl. oz. measure.

Alternatively computed, 2 parts by volume (i.e., "pbv") of the Formaldehyde Solution are intimately mixed with 128 pbv of the pure water to produce 130 pbv of the treating solution.

By another manner of reckoning, the preferred formulation of precisely-constituted treating solution for use in practice of the present invention is one that has and contains (on a weight percent basis) about 0.617%, i.e., generally 0.62%, of the aqueous formaldehyde, in general, as when formulated at about 25° C. This can be calculated by methods well-known in the art. Other types of equivalent expressions are possible as well, e.g., metric units, etc.

There is some slight latitude allowable in the treating solution make-up. Thus, workable preparations may contain as little as 1¾ to as much as 2¼ (to possibly 2½) fl.

oz. of the Formaldehyde Solution added to the 1 gallon quantity of the pure water vehicle: providing, respectively, prepared quantities of 129.75 fl. oz. of made-up treating solution in the former lower-strength-limit case to 130.25 fl. oz. of the preparation in the latter uppermost-strength-limit composition (or as the uppermost possibility indicated, as much as 130.50 or so fl. oz.). By the aforementioned other manner of reckoning, these formulations for use within the scope of the practice of the present invention are those that have and contain (on the weight percent basis) generally about from 0.54% to 0.69% (or even to about 0.77% as corresponds with the 2½ fl. oz value) of the aqueous formaldehyde, in general, as when formulated at about 24° C. Other types of expressions are possible as well, e.g., metric units, etc.

As indicated, essentially pure water is best employed for preparation of the involved treating solutions to be utilized in and for practice of the present invention. As a minimum, the water should be thoroughly de-ionized; with so-called "pyrogen-free" grades of same (of the sort utilized for intraveinous usage) being generally acceptable. Distilled water is also satisfactory; with optimum results and greatest assurance of satisfaction achieved when carefully-collected, and non-contaminated or polluted to even an infinitesimal relative degree, rain water is utilized for preparation of the solutions. In any event, the water used for solution make-up should have excellent characteristics insofar as concerns its being of a totally-"soft" grade or type. In this association, it is preferred to avoid employment of ordinary tap or well water for solution preparation, since in most instances the results obtainable therewith are such as to leave something to be desired with respect to desired treatment effectiveness (unless an unusually-pure source of such sorts of water supply is found and used for the purpose).

The first actual treating procedure in practice of the invention is to very thoroughly wet and soak the external sweaty skin portion of the body to be given the present anti-perspirative remedy hereof and hereunder with prepared treating solution. When extremities are involved, such as and particularly the feet (or, for that matter, even the hands), this is most effectively and efficiently done by actual immersion (or submersion) techniques which are readily accomplished by actually putting the member to be treated in a suitably-contained quantity (as in a pan, bowl or basin, etc.) of the therapeutic solution. For underarm applications, thoroughly-and-excessively-wet swabs or cloth or rag pieces generally suffice for the purpose so long as an effective drenching of the skin area to be treated is thereby achieved. It is also possible to apply the formaldehyde-containing treating solution by means of heavy painting and spraying procedures which are continued as necessary throughout the entire duration of the treatment being made. As has been mentioned, the skin area to be treated should be preliminarily rendered as clean as possible.

Suitable temperatures for application of the treating solution are those in the normal ambient room temperature range; although it may be more comfortable and is satisfactory for the solution to be at body heat and/or in a tepid or luke-warm condition in the process of getting a thoroughly-wetting contact of the skin therewith. Actually, the temperature of the solution at which it is applied is not of particular criticality. It may vary as desired provided it is not so cold or hot, in its extremes, as to be painful or uncomfortable and, especially along this line, as to cause any tissue damage in the area on and to which the treating solution is being applied.

The time of the soaking treatment, however, is rather crucial and of real importance. The skin-wetting with the formaldehyde solution must be continuously done (or made with minimized and insignificant interuptions therein) for at least about 20 or so minutes; preferably for at least half-an-hour. After that, continuation of the soak may be had for as long as may be wanted or tolerated even though prolongation thereof beyond the minimimum time period(s) indicated really does not materially or, in usual cases, even noticably add to the effectiveness or results to be gotten from the treatment. Thus, seldom is the soaking allowed to go on for more than an hour or so.

Following the soaking procedure, the treated skin area must then and immediately thereafter be allowed to throroughly air-dry at ambient room temperature until evaporation of the liquid aqueous vehicle in the treating solution is completed under such conditions. Peculiar and surprising as it may sound and appear, the drying procedure in nothing else but a natural air atmosphere at and under ambient temperature (generally "room" temperature) levels.

Thus, the drying must not and can not be assisted, facilitated or achieved by towel usage or the like and/or with the assistance of such drying means as hot air blowers, radiant or other heaters and/or any other source of artificial heating or absorptive drying means applications. Unless the completely wetted skin area undergoing treatment (such as the feet) are naturally air-dried, the results and effectiveness of the treatment will be found to be seriously impaired and rendered dissatisfactory, as a minimum, and even (as rather generally is the case so-occasioned) completely nullified and rendered worthless for practical purposes insofar as concerns achievement by practice of the present invention of the presently-contemplated and -explained desiderata associated therewith. The reason for this peculiarity escapes practical comprehension and defies pragmatic understanding. However, the air-drying necessity for attainment of all that is so advantageously obtainable in following of the present contribution to the art is a real and factual thing, as off-handedly incredible as the first realization of that may seem.

Properly done treatment in accordance with the present invention provides long-lasting and effective results as regards sweat-problems on the treated superficial skin involved (this having particular and important reference to normally-oderiferous feet so beneficiated). The problems otherwise encountered without treatment are generally completely, or at least to a most significant and very large degree, eliminated for effectively-staying periods to generally include at least about 3 months or about 6 months or more and of up to a year or so—with, in some cases, the desired result lasting as long as 3 or more years—by virtue of the presently revealed therapeutic procedure.

What happens to the treated skin area as a result of practice of the present invention is not completely known or capable of exact explanation. However but without reliance thereon or any implication therefrom in any adverse way as to the effectiveness of or results to be obtained in following of the invention it is thought that the treatment tends to open the involved pores of the skin area subjected to same and to, as an aftermath thereof, keep them in a greater-than-normal open or enlarged condition so as to most beneficially and advantageously allow "breathing" capability and function of and through the treated skin in a relatively free and unconstrained manner whereby and whereupon the normal sort of perspiration with consequent deposit accumulations of same on the sweating skin area involved is precluded and avoided.

In any event, practice of the invention does work; and, at that, work indeed well and fruitfully!

This testimonial-sort of indication of results to be obtained by practice of the invention is based on excellent outcomes of more than 700 actual foot and some other treatments performed as above-explained with 2 fl. oz. to the gallon-strength treating solutions done for test and experimental purposes. Incomprehensible as it appears, identical treatments made on a number of cases with treating solution made up with only 1 fl. oz. of 37% by wt. Formaldehyde Solution to each gallon of rain water were, for all practical purposes, worthless and ineffective for obtention of desired results. In the great preponderance of the testings, problem feet were subjected to the experimentations and probative developmental investigations which, as indicated, became thereby alleviated from and remedied by the described testings. Good results were also had with tests run on the palms of sweaty hands; and are expectable therefor as well as for underarms and other body areas desired to have the benefits of practice of the invention.

Of great significance and reassurance, there were no instances of any damage or irritation to the skin in any of the testings performed. In other words, nothing along such line of a bad or regrettable nature or consequence was thereby caused.

After the treatment and to ensure its longevity to a maximum extent, it is aptly-advisable and prudent to not cover the skin so conditioned with impermeable materials or articles of clothing and/or footwear which hinders or entirely blocks good air ventilation therethrough and as a consequence thereof. Thus, as for treated feet, considerable and relatively prolonged wearing of plastic and/or rubber shoes, galoshes, boots and/or other footwear may prematurely stop the effectiveness of the treatment insofar as relates to its hopefully-expectable good durability. Certain treated leather goods fall in the same category of better-to-avoid garb.

Treatments may be repeated with good effect and without harm or damage coming therefrom in sequence as often as may be desired or necessary as soon as the effectiveness of any given treatment is gone. Along this line, even though it may be desirable and in some cases more efficient to have a trained or experienced person perform any treatment to be given in accordance with the present invention, there is no requirement for same. Home or do-it-yourself treatments, when appropriately performed and all necessary conditions observed and indicated cautions heeded, give entirely acceptable and suitable results and effectiveness. The following of the present invention, as can be discerned in the foregoing, is in all reality simple enough to freely admit of and allow self-treatment therewith and thereby.

It is to be recognized that many immaterial modifications can be readily made in practice of the present invention without substantial departation from it apparent and intended spirit and scope as to embodimentation and practice thereof, all of which is in pursuance and accordance with that which is set forth and delineated in the hereto-appended claims.

What is claimed is:

1. A composition of matter comprised essentially of a solution of formaldehyde in substantially pure water at a formaldehyde concentration from 0.54 percent by weight to 0.69 percent by weight.

2. The composition of claim 1, which consists essentially of said solution.

3. The composition of claim 2, wherein the formaldehyde concentration is about 0.62 percent by weight.

4. The composition of claim 2, wherein the formaldehyde concentration is about but not more than 0.69 percent by weight.

5. The composition of claim 1, which is prepared by mixing with each one U.S. gallon or pro-rata or multiple proportions(s) of substantially pure water from $1\frac{3}{4}$ to $2\frac{1}{4}$ fluid ounces in the English system of measure of 37 percent by weight formaldehyde solution or analogous and corresponding pro-rata or multiple proportion(s) of same.

6. In a method for treating sweaty feet and other superficially exposed non-mucous skin areas of the body, the improvement comprises steps of
 (I) providing a solution consisting essentially of formaldehyde in substantially pure water at a formaldehyde concentration from 0.54 percent by weight to 0.69 percent by weight,
 (II) substantially soaking the skin area to be treated with said solution for at least about twenty minutes, and then
 (III) air-drying at ambient room temperature, in the absence of artificial removal assistance, the skin area subjected to said soaking,
 by steps and under conditions such that adverse consequences of sweating of the skin area, to include excessive sweating and in general unpleasant odor which may accompany the sweating, are substantially eliminated, for a very prolonged period of time, with generally no damage or irritation to the treated skin.

7. The method of claim 6, wherein said soaking is made at a temperature about from ambient room temperature to a luke-warm temperature.

8. The method of claim 6, wherein said soaking is for about from half an hour to an hour.

9. The method of claim 6, wherein the substantially pure water is a deionized "soft" water.

10. The method of claim 6, wherein the substantially pure water is distilled water.

11. The method of claim 6, wherein the substantially pure water is a non-contaminated rain water.

12. The method of claim 6, wherein the formaldehyde concentration is about 0.62 percent by weight.

13. The method of claim 6, wherein the formaldehyde concentration is about but not more than 0.69 percent by weight.

14. The method of claim 6, wherein the very prolonged period of time is at least about 3 months.

15. The method of claim 7, wherein the very prolonged period of time is at least about 3 months.

16. The method of claim 8, wherein the very prolonged period of time is at least about 3 months.

17. The method of claim 9, wherein the very prolonged period of time is at least about 3 months.

18. The method of claim 10, wherein the very prolonged period of time is at least about 3 months.

19. The method of claim 11, wherein the very prolonged period of time is at least about 3 months.

20. The method of claim 12, wherein the very prolonged period of time is at least about 3 months.

21. The method of claim 13, wherein the very prolonged period of time is at least about 3 months.

22. A method useful for treating sweaty feet and other external non-mucous skin area(s) in order to substantially control sweating for a very prolonged period of time thereof comprising serial steps of soaking the feet or other external non-mucous skin area(s) for at least about twenty minutes in a solution provided by mixing with each one U.S. gallon or pro-rata or multiple portion(s) of substantially pure water from 1¾ to 2¼ fluid ounces in the English system of measure of 37 percent by weight Formaldehyde Solution or analogous and corresponding pro-rata or multiple proportion(s) of same, and air drying the feet or other external non-mucous skin area(s) at ambient room temperature in the absence of artificial removal assistance, by steps and under conditions such that sweating of the feet or other external non-mucous skin area(s) is substantially controlled for a very prolonged period of time.

23. The method of claim 22, wherein a step of cleaning the feet or other external non-mucous skin area(s) precedes said soaking step.

24. The method of claim 22, wherein about 2 fluid ounces in the English system of measure of 37 percent by weight Formaldehyde Solution or analogous and corresponding pro-rata or multiple proportion(s) of same is so mixed.

* * * * *